United States Patent
Sawamura

(10) Patent No.: US 12,139,450 B2
(45) Date of Patent: Nov. 12, 2024

(54) CO2 CONVERSION DEVICE

(71) Applicant: eSep Inc., Kyoto (JP)

(72) Inventor: Kenichi Sawamura, Kyoto (JP)

(73) Assignee: eSep Inc., Souraku-gun (JP)

( * ) Notice: Subject to any disclaimer, the term of this patent is extended or adjusted under 35 U.S.C. 154(b) by 0 days.

(21) Appl. No.: 18/560,517

(22) PCT Filed: May 13, 2022

(86) PCT No.: PCT/JP2022/020290
§ 371 (c)(1),
(2) Date: Nov. 13, 2023

(87) PCT Pub. No.: WO2022/239873
PCT Pub. Date: Nov. 17, 2022

(65) Prior Publication Data
US 2024/0246893 A1    Jul. 25, 2024

(30) Foreign Application Priority Data

May 13, 2021    (JP) .................................. 2021-081995

(51) Int. Cl.
*C07C 29/152* (2006.01)
*B01D 71/02* (2006.01)
(Continued)

(52) U.S. Cl.
CPC ........ *C07C 29/152* (2013.01); *B01D 71/0281* (2022.08); *B01J 8/009* (2013.01);
(Continued)

(58) Field of Classification Search
None
See application file for complete search history.

(56) References Cited

U.S. PATENT DOCUMENTS

2004/0064002 A1 *  4/2004  Lee ..................... C07C 41/09
                                              568/698
2005/0038129 A1    2/2005  Shikada
                            (Continued)

FOREIGN PATENT DOCUMENTS

CA        2186222 A       10/1995
CN    102584526 A    *    7/2012
                            (Continued)

OTHER PUBLICATIONS

Diban et al. Influence of the membrane properties on the catalytic production of dimethyl ether with in situ water removal for the successful capture of co2. Chemical Engineering Journal 234 (2013) 140-148. (Year: 2013).*

(Continued)

*Primary Examiner* — Jennifer A Leung
(74) *Attorney, Agent, or Firm* — Muncy, Geissler, Olds & Lowe, P.C.

(57) ABSTRACT

A $CO_2$ conversion device reacts $CO_2$ and hydrogen as raw materials to be converted to methanol or dimethyl ether, in which a methanol synthesis catalyst and a methanol conversion catalyst are disposed with the separation membrane, and methanol and water are produced from $CO_2$ and hydrogen by the methanol synthesis catalyst disposed on a high pressure side via the separation membrane, and then the produced methanol and water from a reaction system containing $CO_2$ and hydrogen are selectively subjected to membrane-permeation through the separation membrane, and a mixture of methanol, dimethyl ether, and water is obtained by the methanol conversion catalyst disposed on a low pressure side via the separation membrane.

7 Claims, 1 Drawing Sheet

(51) Int. Cl.
*B01J 8/00* (2006.01)
*C01B 39/38* (2006.01)
*C07C 31/04* (2006.01)
*C07C 41/09* (2006.01)
*C07C 43/04* (2006.01)

(52) U.S. Cl.
CPC .............. *C01B 39/38* (2013.01); *C07C 31/04* (2013.01); *C07C 41/09* (2013.01); *C07C 43/043* (2013.01)

(56) References Cited

U.S. PATENT DOCUMENTS

| | | | |
|---|---|---|---|
| 2006/0052647 | A1 | 3/2006 | Shikada |
| 2014/0336420 | A1 | 11/2014 | Iijima |
| 2014/0360939 | A1 | 12/2014 | Yamada et al. |
| 2016/0176775 | A1 | 6/2016 | Gruetzner et al. |
| 2018/0016218 | A1* | 1/2018 | Klinghoffer ......... B01J 37/0215 |
| 2021/0046442 | A1* | 2/2021 | Goetheer .............. C07C 29/152 |

FOREIGN PATENT DOCUMENTS

| | | |
|---|---|---|
| JP | 9-511509 A | 11/1997 |
| JP | 9-309850 A | 12/1997 |
| JP | 2000-157851 A | 6/2000 |
| JP | 2011-51975 A | 3/2011 |
| JP | 2013-112769 | 6/2013 |
| JP | 2015-44926 A | 3/2015 |
| JP | 5863421 B2 | 2/2016 |
| JP | 2016-117726 A | 6/2016 |
| JP | 6338218 B2 | 6/2018 |
| JP | 2021-24801 A | 2/2021 |
| WO | 2013/125661 A1 | 8/2013 |

OTHER PUBLICATIONS

Li et al. Review: High Temperature Water Permeable Membrane Reactors for CO2 Utilization. Chemical Engineering Journal 420 ( 2021) 129834. (Year: 2021).*

Huazheng Li et al., Na-gated water-conducting nanochannels for boosting CO2 conversion to liquid fuels, Science 367, 667-671, (2020).

Huazheng Li et al., The high-yield direct synthesis of dimethyl ether from CO2 and H2 in a dry reaction environment, Journal of Materials Chemistry A, 9, 2678-2682 (2021).

Sawamura, Kenichi et al., SCEJ 38th Spring Meeting, "Separation of polar molecules/inorganic gases at high temperature based on ZSM-5 membrane".

Sawamura, Kenichi et al. SCEJ 39th Autumn Meeting, "Effect of methanol adsorption on ZSM-5 membrane on hydrogen permeation".

Sawamura K et al., Reverse-Selective Microporous Membrane for Gas Separation, Chem. Asian J., 2009, 4, 1070-1077.

* cited by examiner

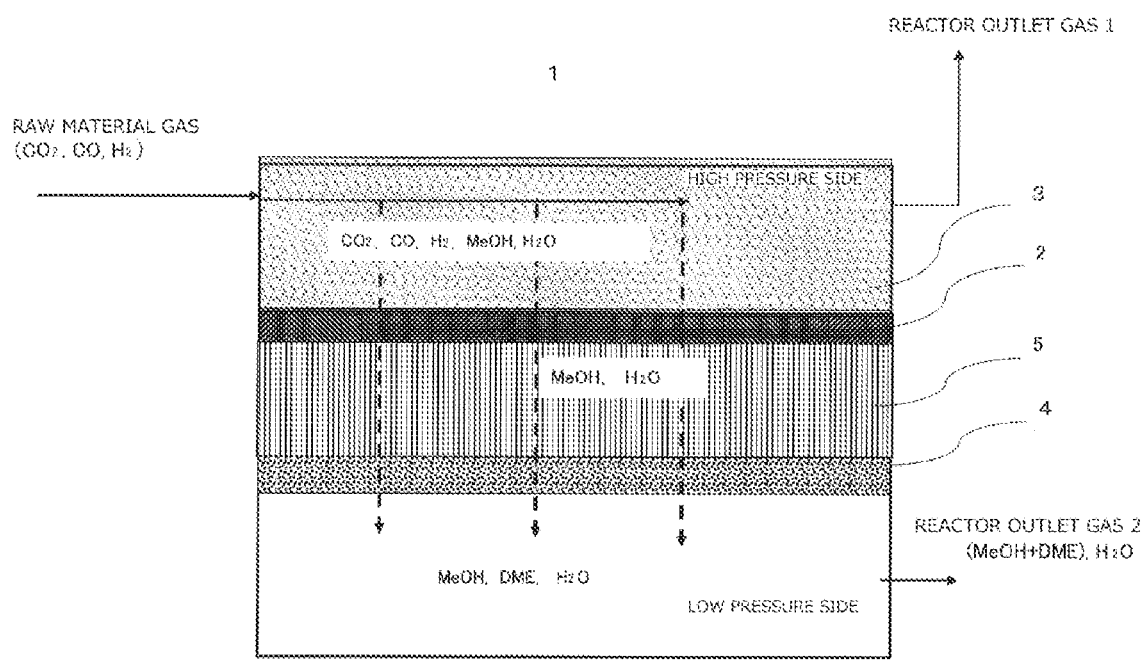

CO2 CONVERSION DEVICE

TECHNICAL FIELD

The present invention relates to a $CO_2$ conversion device for reacting carbon dioxide ($CO_2$) with hydrogen to be converted to methanol (MeOH) or dimethyl ether (DME).

BACKGROUND ART

With the aim of achieving carbon neutrality by 2050, green technology development investment for carbon neutral has accelerated worldwide from 2020, and the business environment has changed in most fields such as automobiles, chemistry, environment, and energy. There is an urgent need to develop or improve new methods for synthesizing chemicals and fuels derived from carbon neutral renewable biomass or using recovered $CO_2$ as a raw material, rather than fossil resources such as natural gas and coal. As shown in the following reaction, for conventional raw materials derived from fossil resources, a synthesis (Formula 1) via a synthesis gas which is a mixed gas of carbon monoxide (CO) and hydrogen is mainly used, but in a case where $CO_2$ is used as a raw material, it is necessary to particularly consider Formulae 2 to 4.

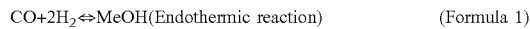

CO+2H$_2$⇌MeOH(Endothermic reaction)　　(Formula 1)

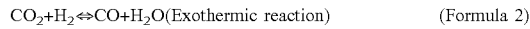

CO$_2$+H$_2$⇌CO+H$_2$O(Exothermic reaction)　　(Formula 2)

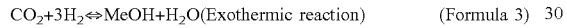

CO$_2$+3H$_2$⇌MeOH+H$_2$O(Exothermic reaction)　　(Formula 3)

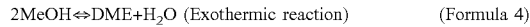

2MeOH⇌DME+H$_2$O (Exothermic reaction)　　(Formula 4)

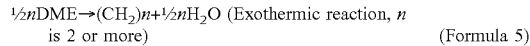

½nDME→(CH$_2$)n+½nH$_2$O (Exothermic reaction, n is 2 or more)　　(Formula 5)

Formulae 1 to 4 are equilibrium reactions, but Formula 5 is not subject to equilibrium constraints. Therefore, once conversion is performed until DME is obtained, an existing technique can be used as a technique for conversion to olefins or gasoline having 2 or more carbon atoms. When DME is converted to olefins, gasoline, or the like by Formula 5, the conversion to DME from MeOH is promoted by Formula 4. Therefore, a process in which a mixture of MeOH and DME is obtained from $CO_2$ is determined to be a current bottleneck process.

For example, in Patent Literature 1, a method for producing gasoline or dimethyl ether via methanol by utilizing exhaust heat with high efficiency, in which a $CO_2$ recovery device is also used is disclosed. On the other hand, a raw material to be used is natural gas, and in a case where biomass containing a large amount of $CO_2$ or recovered $CO_2$ is used as a raw material, it is difficult to apply the method as it is.

In Patent Literature 2, a method for producing hydrocarbons having 2 or more carbon atoms via methanol by reacting $CO_2$ with hydrogen is described. However, a $CO_2$ conversion rate is as low as about 20%, and further improvement is required.

In Patent Literature 3, a method for developing a novel catalyst in which a methanol synthesis catalyst and a methanol conversion catalyst are combined to improve a conversion rate of $CO_2$, and producing hydrocarbons having 2 or more carbon atoms from a mixed gas containing $CO_2$ and hydrogen is described.

However, 65% or more of products obtained by $CO_2$ conversion is CO, and a yield of intended hydrocarbons having 2 or more carbon atoms is as low as less than 10%.

In Non Patent Literature 1 and 2, by selectively subjecting only water to membrane-permeation through a separation membrane from a reaction system using $CO_2$ and hydrogen as raw materials, and promoting production of MeOH in Formula 3 and production of DME in Formula 4, significant performance improvements to a $CO_2$ conversion rate of 83% and a DME yield of 54.5% have been reported. On the other hand, even total yield of MeOH and DME is about 60%, and further improved performance is essential in view of practical application.

CITATION LIST

Patent Literature

Patent Literature 1: JP 5863421 B2
Patent Literature 2: JP 2015-44926 A
Patent Literature 3: JP 6338218 B2

Non Patent Literature

Non Patent Literature 1: Li et al., Science 367, 667-671 (2020).
Non Patent Literature 2: Li et al., J. Mater. Che. A, 9, 2678-2682 (2021).

SUMMARY OF INVENTION

Technical Problem

In a synthesis of chemical products or fuels using $CO_2$ as a raw material, consuming a large amount of energy in a process of the synthesis is an incorrect priority from the viewpoint of carbon neutrality, and further energy saving and increase in efficiency are required.

Also for the bottleneck process in which a mixture of MeOH and DME is obtained from $CO_2$, it is essential to design and develop a system capable of achieving a $CO_2$ conversion rate of 90% or more and a total yield of MeOH and DME of 80% or more, preferably a yield of 90% or more.

An object of the present invention is to provide a production system capable of converting $CO_2$ and hydrogen into a methanol and dimethyl ether mixture, desirably with a high yield of almost 90% or more.

Solution to Problem

In order to achieve the above object, Aspect (1) is a $CO_2$ conversion device that reacts $CO_2$ and hydrogen as raw materials to be converted to methanol or dimethyl ether, the $CO_2$ conversion device including: a methanol synthesis catalyst: a methanol conversion catalyst; and a separation membrane, in which the methanol synthesis catalyst and the methanol conversion catalyst are disposed with the separation membrane therebetween, and methanol and water are produced from $CO_2$ and hydrogen by the methanol synthesis catalyst disposed on a high pressure side via the separation membrane, and then the produced methanol and water are selectively subjected to membrane-permeation from a reaction system containing $CO_2$ and hydrogen by the separation membrane, and a mixture of methanol, dimethyl ether, and water is obtained by the methanol conversion catalyst disposed on a low pressure side via the separation membrane.

Aspect (2) is the $CO_2$ conversion device according to Aspect (1), in which the separation membrane is a ZSM-5 type zeolite membrane having a Si/Al ratio of 10 to 20, and metal cations that selectively adsorb methanol and water with respect to $CO_2$ or hydrogen are immobilized on an exchange cation site of Al in a zeolite framework.

Aspect (3) is the $CO_2$ conversion device according to Aspect (1) or (2), in which a support of the separation membrane separating the methanol synthesis catalyst and the methanol conversion catalyst is a porous α-alumina substrate having a porosity of 25% to 55%.

Aspect (4) is the $CO_2$ conversion device according to any one of Aspects (1) to (3), in which carbon monoxide is further added to $CO_2$ and hydrogen as a raw material.

Aspect (5) is an olefin and/or gasoline production system using the $CO_2$ conversion device according to any one of Aspects (1) to (4).

Advantageous Effects of Invention

According to Aspect (1), the methanol that has permeated through the separation membrane is converted to DME, so that a methanol partial pressure difference via the membrane is increased and permeation of methanol is promoted, and as a result, a conversion reaction of $CO_2 \rightarrow MeOH \rightarrow DME$ in accordance with Formulae 3 and 4 is also promoted, and an effect that a single-stream yield of a target product (MeOH+DME) can be improved to about 90% or more even from a $CO_2$ raw material is exhibited.

According to Aspect (2), both effects that methanol and water can be selectively subjected to membrane-permeation from a reaction system at 200° C. to 300° C. in approximately equimolar amounts from a mixed gas containing $CO_2$ and hydrogen and high membrane durability is obtained can be exhibited.

According to Aspect (3), effects that the support of the separation membrane has both high pressure resistance and a heat insulating property, and while a temperature of a methanol synthesis catalyst layer is maintained at 220° C. to 280° C., a temperature of a subsequent processes after the methanol conversion catalyst layer can be maintained in a higher temperature state by heat generated by the reaction of Formula 4 are exhibited. Effects that a reaction temperature at which olefin or gasoline is synthesized from DME shown in Formula 5 is generally 300° C. to 450° C., and a mixed gas of MeOH and DME can be preheated to about 300° C. without inputting external heat energy, by reaction heat generated by the conversion from MeOH to DME in Formula 4 are exhibited. According to Aspect (4), by adding carbon monoxide to $CO_2$ and hydrogen as a raw material, an effect of further increasing a single-stream yield of a target product (MeOH+DME) is exhibited.

According to Aspect (5), by using the $CO_2$ conversion device according to any one of Aspects (1) to (4), an effect of increasing the single-stream yield of (MeOH+DME) in a bottleneck process and increasing the production efficiency of the olefin and/or gasoline production system is exhibited.

BRIEF DESCRIPTION OF DRAWINGS

FIG. 1 is a schematic view showing an embodiment of a $CO_2$ conversion device of the present disclosure.

DESCRIPTION OF EMBODIMENTS

Next, embodiments of the present disclosure will be described with reference to the drawings, but the present disclosure is not limited thereto.

Referring to FIG. 1, a $CO_2$ conversion device of the present disclosure is a $CO_2$ conversion device 1 that mainly uses a mixed gas of $CO_2$ and hydrogen (or a gas to which CO is further added) as a raw material, and reacts $CO_2$ and hydrogen (or reacts CO and hydrogen) to be converted to methanol or dimethyl ether, in which a methanol synthesis catalyst 3 and a methanol conversion catalyst 4 are disposed with a separation membrane 2 therebetween supported by a support 5. Methanol (MeOH) and water ($H_2O$) are produced from $CO_2$ and hydrogen by the methanol synthesis catalyst 2 disposed on a high pressure side of 3 to 7 MPa through the separation membrane 2, and then produced methanol and water from a reaction system containing $CO_2$ and hydrogen are selectively subjected to membrane-permeation through the separation membrane 2 at 220° C. to 280° C., and a mixture of methanol, dimethyl ether, and water (MeOH, DME, and $H_2O$) is obtained at 250° C. to 400° C. by the methanol conversion catalyst 4 disposed on a low pressure side of 0.5 MPa or less, and discharged from a reactor outlet gas 2. The discharged mixture is further converted to, for example, olefins or gasoline. Although a space (produced gas flow path) for the mixture obtained by the reaction is illustrated on the low pressure side, a gap (raw material gas flow path) may be provided above the methanol synthesis catalyst 3, on the high pressure side, and the raw material gas may be supplied to the methanol synthesis catalyst 3 via the raw material gas flow path, or the $CO_2$ conversion device of the present disclosure may be placed in a module housing, and the raw material gas may pass between the housing and the $CO_2$ conversion device. In addition, although not illustrated here, in order to operate the device, a device for supplying a mixed gas of $CO_2$ and hydrogen as raw materials, a pressure adjusting device, a temperature control device, and the like are required.

Here, as the methanol synthesis catalyst 3, a known catalyst such as a copper-zinc-based catalyst and the like can be used, and general optimum operation conditions are in ranges of 3 to 7 MPa and 220° C. to 280° C. In addition, as a methanol conversion catalyst 5, a known catalyst such as an aluminosilicate zeolite-based catalyst or the like can be used, and MeOH can be converted to DME in ranges of 0.5 MPa or less and 250° C. to 400° C. The $CO_2$ conversion device of the present disclosure can be used in an olefin or gasoline production system for producing olefins or gasoline. Therefore, assuming further conversion to olefins or gasoline, it is desirable to obtain a mixture of MeOH, DME, and water in order to alleviate catalyst deterioration. When DME is converted from MeOH to gasoline at once, a hot spot is locally formed due to rapid heat generation, and catalyst deterioration is accelerated. Therefore, it is desirable that MeOH is converted to DME to some extent before conversion to olefins or gasoline, and reaction heat is controlled and adjusted. Here, a known catalyst such as an H-SAPO type zeolite catalyst for the conversion to olefins and an H-ZSM-5 type zeolite catalyst for the conversion to gasoline can be used, and the operation temperature thereof is 300° C. to 450° C. Therefore, it is desirable to preheat the mixed gas of MeOH and DME to 300° C. or higher without inputting external heat energy by reaction heat generated at the time of conversion from MeOH to DME. In addition, moisture has an effect of suppressing carbon deposition on a catalyst, and on the other hand, a high temperature of 450° C. or higher causes catalyst deterioration, so that only water vapor can be separated and removed by a separation membrane as necessary to adjust a moisture concentration thereof. In addition to a method of disposing the methanol conversion catalyst 5 as a fixed layer, the methanol conversion catalyst 5 can also be disposed as a fluidized layer in order to facilitate catalyst regeneration.

The methanol synthesis catalyst 3 is also appropriately selected and disposed according to usage such as filling in a powder form or sintering in a slurry form.

Here, as the separation membrane 2 used in the present disclosure, a zeolite membrane having excellent durability can be used. The zeolite membrane is desirably a ZSM-5 type zeolite membrane. From the viewpoint of membrane durability and methanol-water permeation separation performance, it is desirable that metal cations such as Li, Na, and K that selectively adsorb methanol and water with respect to $CO_2$ or hydrogen are immobilized on an exchange cation site of Al in a zeolite framework. The zeolite membrane desirably has a Si/Al ratio of 10 to 20. The zeolite membrane is desirably a ZSM-5 type zeolite membrane having a Si/Al ratio of 10 to 20. When the Si/Al ratio is too low, the membrane durability is poor, and when the Si/Al ratio is too high, the separation selectivity of methanol and water with respect to $CO_2$ and hydrogen is not exhibited. In addition, also in a case where metal cations are not immobilized on the exchange cation site of Al in the zeolite framework, the separation selectivity of methanol and water with respect to $CO_2$ and hydrogen is not exhibited. The separation selectivity of methanol and water with respect to $CO_2$ and hydrogen is desirably 30 or more, 40 or more, or 50) or more. With such a configuration, it is possible to suppress leakage of $CO_2$ or hydrogen serving as the raw material gas from becoming too large, and it is easy to obtain a predetermined effect. In addition, for the A type zeolite membrane used in Non Patent Literature 1 and 2, it is preferable to use a ZSM-5 type zeolite membrane as the separation membrane because water permeates but methanol hardly permeates the membrane, and membrane durability is not sufficient. For example, with a ZSM-5 type zeolite membrane having a Si/Al ratio of 10 to 20 in which Na cations are immobilized on an exchange cation site of Al in a zeolite framework, it is possible to obtain a separation selectivity of methanol and water with respect to $CO_2$ and hydrogen of 30 or more, 40 or more, or 50 or more and a methanol permeability of $10^{-7}$ [mol/(m² s Pa)] or more and a water permeability of $10^{-7}$ [mol/(m² s Pa)] or more, in a high temperature condition of 200° C. to 300° C.

A thickness of the separation membrane is preferably 0.5 to 10 μm, and more preferably 1 to 5 μm.

From another viewpoint, it is preferable that the separation membrane has a lower limit of the membrane permeability of methanol of $2\times10^{-8}$ [mol/(m² s Pa)] or more, $3\times10^{-8}$ [mol/(m² s Pa)] or more, $5\times10^{-8}$ [mol/(m² s Pa)] or more, or $8\times10^{-8}$ [mol/(m² s Pa)] or more.

It is preferable that the separation membrane has (membrane permeability of water)/(membrane permeability of methanol) of 2.0 or less, 1.5 or less, 1.3 or less, or 1.2 or less. The lower limit is not particularly limited, but is 0.5 or more, 0.8 or more, or 1.0 or more.

The separation membrane permeability of each component can be adjusted by the Si/Al ratio, the type of metal cation, an amount of the immobilized metal cation, and the like.

As the support 5 of the separation membrane 2 used in the present disclosure, a porous α-alumina substrate having a porosity of 45% to 55% and excellent in heat insulating properties in addition to pressure resistance is preferable. When the porosity is less than 25%, while the pressure resistance is excellent, the heat insulating properties and the membrane permeability are deteriorated more than necessary. When the porosity is more than 55%, there is a concern that the pressure resistance is lowered, and the separation membrane 2 is damaged due to the pressure difference through the membrane. In the $CO_2$ conversion device of the present disclosure, while a temperature of a methanol synthesis catalyst layer is maintained at 220° C. to 280° C., a temperature of a subsequent steps after the methanol conversion catalyst layer can be maintained in a higher temperature state by heat generated by the reaction of Formula 4. Effects that a reaction temperature at which olefin or gasoline is synthesized from DME shown in Formula 5 is generally 300° C. to 450° C., and by using a support of the separation membrane excellent in heat insulating properties, a mixed gas of MeOH and DME can be preheated to about 300° C. without inputting external heat energy, by reaction heat generated by the conversion from MeOH to DME in Formula 4 are exhibited. A generally used support such as SiC having high thermal conductivity is not suitable as a support of the separation membrane 2 of the present disclosure because it is difficult to maintain a temperature difference between a methanol synthesis catalyst layer and a methanol conversion catalyst layer. In addition, a tubular support is generally used as a shape of the support, and a support having a diameter of 1 to 1.6 cm and a length of 40 to 120 cm is preferable from the viewpoint of durability and economic efficiency. When the support is tubular, a basic part ($CO_2$ conversion module) of the $CO_2$ conversion device of the present disclosure is also tubular. A schematic view of FIG. 1 is a partial cross-sectional view of a cross section passing through a central axis of a tubular support and taken along an axial direction thereof. In this case, the separation membrane 2 is disposed on an outer peripheral side of the support, and the low pressure side is a hollow portion of the support.

A thickness of the support is preferably 1 to 3 mm, and more preferably 1 to 2 mm.

An aspect of the present disclosure is a $CO_2$ conversion device that reacts $CO_2$ and hydrogen as raw materials to be converted to methanol or dimethyl ether. The $CO_2$ conversion device includes:

a $CO_2$ conversion module including
a separation membrane that allows methanol and water to selectively permeate therethrough;
a methanol synthesis catalyst layer which is provided on one side of the separation membrane and produces methanol and water from $CO_2$ and hydrogen; and
a methanol conversion catalyst layer that is provided on the other side of the separation membrane and converts at least a part of methanol to dimethyl ether; and
a raw material supply means for supplying a raw material gas containing $CO_2$ and hydrogen to one side of the separation membrane at a pressure higher than a pressure on the other side of the separation membrane.

Another aspect of the present disclosure is a $CO_2$ conversion module.

The $CO_2$ conversion module includes:
a separation membrane that allows methanol and water to selectively permeate therethrough;
a methanol synthesis catalyst layer which is provided on one side of the separation membrane and produces methanol and water from $CO_2$ and hydrogen; and
a methanol conversion catalyst layer that is provided on the other side of the separation membrane and converts at least a part of methanol into dimethyl ether.

Next, Examples of the present disclosure will be described, but the present disclosure is not limited to these examples.

EXAMPLES

A feed gas composition (CO, $CO_2$, and $H_2$), membrane permeability ($H_2$, CO, $CO_2$, $H_2O$, MeOH, and DME), a catalyst arrangement (a MeOH conversion catalyst and a MeOH synthesis catalyst), an operating condition on a high pressure side (temperature and pressure), and an operating condition on a low pressure side (temperature and pressure) were varied, and a conversion rate and carbon balance between a reactor outlet gas 1 (residue) and a reactor outlet gas 2 (target product) were calculated by process simulation. In the process simulation, a region of the separation membrane used in a target separation process can be divided into 10000 to 10 billion cells, and a reaction amount and a membrane permeation amount in each divided cell can be calculated by sequential calculation. As an analysis precondition, an analysis was performed under isothermal and isobaric conditions with respect to the flow direction in order to speed up (simplify) the analysis process. The membrane area of the separation membrane was fixed at 45 $m^2$, with a sufficient amount of the catalyst to reach equilibrium for each divided cell, the analysis was performed. The feed gas composition, the membrane permeability, the catalyst arrangement, and the operating conditions are shown in Table 1, and the analysis results are shown in Table 2.

The number of cell divisions of the separation membrane: 10 billion

Analysis software: "eSepMR-Methanol Synthesis" series manufactured by eSep Co., Ltd.

MeOH conversion catalyst: ZSM-5 type zeolite, imitation of model number 822 HOD1A, manufactured by Tosoh Corporation MeOH synthesis catalyst: imitation of a $Cu/Zn/Al_2O_3$ catalyst manufactured by Thermo Fisher Scientific Material of separation membrane: imitation of ZSM-5 type zeolite (Si/Al ratios of Examples 1-1, 1-2, 1-3, 1-6, 1-7, 1-8, 1-9, and 1-10 correspond to 12), model number 822 HOA (ion-exchanged into sodium type) manufactured by Tosoh Corporation

TABLE 1

| | Feed Gas [mol/s] | | | Membrane Permeability [$10^{-9}$ mol/($m^2$ s Pa)] | | | | | | Catalyst Disposition | | Operating Condition on High Pressure Side | | Operating Condition on Low Pressure Side | |
|---|---|---|---|---|---|---|---|---|---|---|---|---|---|---|---|
| | CO | CO2 | H2 | H2 | CO | CO2 | H2O | MeOH | DME | High Pressure Side | Low Pressure Side | Temperature [° C.] | Pressure [MPa] | Temperature [° C.] | Pressure [MPa] |
| Example 1-1 | 0 | 1 | 3 | 1 | 0.5 | 0.5 | 100 | 100 | 1 | MeOH Synthesis Catalyst | MeOH Conversion Catalyst | 250 | 5.0 | 250 | 0.1 |
| Example 1-2 | 0.5 | 0.5 | 3 | 1 | 0.5 | 0.5 | 100 | | | | | | | | |
| Example 1-3 | 0.9 | 0.1 | 3 | 1 | 0.5 | 0.5 | 100 | | | | | | | | |
| Example 1-4 | 0 | 1 | 3 | 2 | 1 | 1 | 100 | | | | | | | | |
| Example 1-5 | 0 | 1 | 3 | 2 | 1 | 1 | 200 | | | | | | | | |
| Example 1-6 | 0 | 1 | 3 | 1 | 0.5 | 0.5 | 100 | 100 | 1 | MeOH Synthesis Catalyst | MeOH Conversion Catalyst | 230 | 5.5 | 260 | 0.1 |
| Example 1-7 | | | | | | | | | | | | 240 | 5.5 | 280 | 0.1 |
| Example 1-8 | | | | | | | | | | | | 250 | 5.5 | 300 | 0.1 |
| Example 1-9 | | | | | | | | | | | | 250 | 5.5 | 310 | 0.2 |
| Example 1-10 | | | | | | | | | | | | 260 | 6.0 | 320 | 0.3 |
| Example 2-1 | 0 | 1 | 3 | — | — | — | — | — | — | MeOH Synthesis Catalyst and MeOH Conversion Catalyst | None | 250 | 5.0 | 250 | 0.1 |
| Example 2-2 | 0.5 | 0.5 | 3 | — | — | — | — | — | — | | | | | | |
| Example 2-3 | 0.9 | 0.1 | 3 | — | — | — | — | — | — | | | | | | |
| Example 2-4 | 0 | 1 | 3 | 1 | 0.5 | 0.5 | 199 | 1 | 1 | | | | | | |
| Example 2-5 | 0.5 | 0.5 | 3 | 1 | 0.5 | 0.5 | 199 | 1 | 1 | | | | | | |
| Example 2-6 | 0.9 | 0.1 | 3 | 1 | 0.5 | 0.5 | 199 | 1 | 1 | | | | | | |
| Example 2-7 | 0 | 1 | 3 | 1 | 0.5 | 0.5 | 190 | 10 | 1 | | | | | | |
| Example 2-8 | 0.5 | 0.5 | 3 | 1 | 0.5 | 0.5 | 190 | 10 | 1 | | | | | | |
| Example 2-9 | 0.9 | 0.1 | 3 | 1 | 0.5 | 0.5 | 190 | 10 | 1 | | | | | | |
| Example 2-10 | 0 | 1 | 3 | 1 | 0.5 | 0.5 | 100 | 100 | 1 | | | | | | |
| Example 2-11 | 0.5 | 0.5 | 3 | 1 | 0.5 | 0.5 | 100 | 100 | 1 | | | | | | |
| Example 2-12 | 0.9 | 0.1 | 3 | 1 | 0.5 | 0.5 | 100 | 100 | 1 | | | | | | |
| Example 2-13 | 0 | 1 | 3 | 1 | 0.5 | 0.5 | 100 | 100 | 1 | MeOH Synthesis Catalyst and MeOH Conversion Catalyst | MeOH Conversion Catalyst | | | | |
| Example 2-14 | 0.5 | 0.5 | 3 | 1 | 0.5 | 0.5 | 100 | 100 | 1 | | | | | | |
| Example 2-15 | 0.9 | 0.1 | 3 | 1 | 0.5 | 0.5 | 100 | 100 | 1 | | | | | | |
| Example 2-16 | 0 | 1 | 3 | 1 | 0.5 | 0.5 | 190 | 10 | 1 | MeOH Synthesis Catalyst | MeOH Conversion Catalyst | | | | |
| Example 2-17 | 0.5 | 0.5 | 3 | 1 | 0.5 | 0.5 | 190 | 10 | 1 | | | | | | |
| Example 2-18 | 0.9 | 0.1 | 3 | 1 | 0.5 | 0.5 | 190 | 10 | 1 | | | | | | |
| Example 2-19 | 0 | 1 | 3 | 1 | 0.5 | 0.5 | 150 | 50 | 1 | | | | | | |
| Example 2-20 | 0.5 | 0.5 | 3 | 1 | 0.5 | 0.5 | 150 | 50 | 1 | | | | | | |
| Example 2-21 | 0.9 | 0.1 | 3 | 1 | 0.5 | 0.5 | 150 | 50 | 1 | | | | | | |
| Example 2-22 | 0 | 1 | 3 | 5 | 2.5 | 2.5 | 100 | 100 | 1 | | | | | | |
| Example 2-23 | 0 | 1 | 3 | 10 | 5 | 5 | 100 | 100 | 1 | | | | | | |

(Analysis Conditions)

TABLE 2

| | CO Conversion Rate [%] | CO2 Conversion Rate [%] | Carbon Balance Between Reactor Outlet Gases 1 and 2 (Total) [%] | | | | | |
|---|---|---|---|---|---|---|---|---|
| | | | CO | CO2 | MeOH | DME | Residue (CO + CO2) | Target Product (MeOH + DME) |
| Example 1-1 | — | 92.0 | 1.0 | 8.0 | 21.9 | 69.1 | 9.0 | 91.0 |
| Example 1-2 | 99.3 | 97.8 | 0.4 | 1.1 | 14.1 | 84.4 | 1.5 | 98.5 |
| Example 1-3 | 99.6 | 97.6 | 0.4 | 0.2 | 10.5 | 88.9 | 0.6 | 99.4 |
| Example 1-4 | — | 90.7 | 1.1 | 9.3 | 20.7 | 68.9 | 10.4 | 89.6 |
| Example 1-5 | — | 92.9 | 1.1 | 7.1 | 21.6 | 70.2 | 8.2 | 91.8 |
| Example 1-6 | — | 95.1 | 0.4 | 4.9 | 22 | 72.7 | 5.3 | 94.7 |
| Example 1-7 | — | 95.6 | 0.4 | 4.4 | 19.9 | 75.3 | 4.8 | 95.2 |
| Example 1-8 | — | 95.6 | 0.5 | 4.4 | 23 | 72.1 | 4.9 | 95.1 |
| Example 1-9 | — | 94.7 | 0.5 | 5.3 | 26 | 68.2 | 5.8 | 94.2 |
| Example 1-10 | — | 93.3 | 0.8 | 6.7 | 29.9 | 62.6 | 7.5 | 92.5 |
| Example 2-1 | — | 32.9 | 3.5 | 67.1 | 5.4 | 24.0 | 70.6 | 29.4 |
| Example 2-2 | 91.7 | 18.7 | 4.2 | 40.6 | 6.7 | 48.5 | 44.8 | 55.2 |
| Example 2-3 | 92.5 | 8.5 | 6.7 | 9.1 | 9.0 | 75.2 | 15.8 | 84.2 |
| Example 2-4 | — | 84.5 | 3.2 | 15.5 | 2.6 | 78.7 | 18.7 | 81.3 |
| Example 2-5 | 95.7 | 86.6 | 2.1 | 6.7 | 2.7 | 88.5 | 8.8 | 91.2 |
| Example 2-6 | 98.2 | 69.6 | 1.6 | 3.0 | 2.7 | 92.7 | 4.6 | 95.4 |
| Example 2-7 | — | 85.3 | 3.0 | 14.7 | 7.2 | 75.1 | 17.7 | 82.3 |
| Example 2-8 | 96.1 | 88.0 | 2.0 | 6.0 | 7.0 | 85.0 | 8.0 | 92.0 |
| Example 2-9 | 98.3 | 74.3 | 1.5 | 2.6 | 6.5 | 89.4 | 4.1 | 95.9 |
| Example 2-10 | — | 87.7 | 2.0 | 12.3 | 41.2 | 44.5 | 14.3 | 85.7 |
| Example 2-11 | 97.7 | 93.6 | 1.1 | 3.2 | 38.6 | 57.1 | 4.3 | 95.7 |
| Example 2-12 | 99.0 | 91.1 | 0.9 | 0.9 | 30.3 | 67.9 | 1.8 | 98.2 |
| Example 2-13 | — | 88.6 | 1.8 | 11.4 | 15.4 | 71.4 | 13.2 | 86.8 |
| Example 2-14 | 98.1 | 94.9 | 0.9 | 2.6 | 12.4 | 84.1 | 3.5 | 96.5 |
| Example 2-15 | 99.2 | 94.7 | 0.7 | 0.5 | 8.5 | 90.3 | 1.2 | 98.8 |
| Example 2-16 | — | 58.6 | 15.6 | 41.4 | 30.0 | 13.0 | 57.0 | 43.0 |
| Example 2-17 | 66.9 | 43.3 | 16.6 | 28.3 | 33.5 | 21.6 | 44.9 | 55.1 |
| Example 2-18 | 79.9 | 14.3 | 18.1 | 8.6 | 36.6 | 36.7 | 26.7 | 73.3 |
| Example 2-19 | — | 80.0 | 4.6 | 20.0 | 22.9 | 52.5 | 24.6 | 75.4 |
| Example 2-20 | 96.1 | 90.2 | 1.9 | 4.9 | 19.1 | 74.1 | 6.8 | 93.2 |
| Example 2-21 | 99.2 | 95.3 | 0.7 | 0.5 | 10.3 | 88.5 | 1.2 | 98.8 |
| Example 2-22 | — | 81.0 | 2.3 | 19.0 | 15.5 | 63.2 | 21.3 | 78.7 |
| Example 2-23 | — | 69.9 | 3.7 | 30.1 | 13.7 | 52.5 | 33.8 | 66.2 |

Examples 1-1 to 1-10 are performed in excerpted conditions under which a yield of MeOH+DME as a target product can be achieved by about 90%, in the embodiment of the $CO_2$ conversion system of the present disclosure shown in FIG. 1.

Examples 2-1 to 2-3 are cases where a MeOH synthesis catalyst and a MeOH conversion catalyst were disposed under the same atmosphere without using a separation membrane in Examples 1-1 to 1-3, respectively, and a yield of MeOH+DME as a target product was significantly reduced as the $CO_2$ concentration in the raw material gas increased.

Examples 2-4 to 2-6 correspond to the optimization of the method used in Non Patent Literature 1 and 2, and an attempt was made to promote the production of MeOH in Formula 3 and the production of DME in Formula 4 by selectively subjecting only water to membrane-permeation through the separation membrane by installing a dehydration membrane in Examples 2-1 to 2-3. Although the yield of MeOH+DME was significantly improved as compared to Examples 2-1 to 2-3, in a case where the feed gas of Example 2-4 was a raw material containing only $CO_2$ and hydrogen and not containing CO (hereinafter, it is referred to as a $CO_2$ raw material), the yield of MeOH+DME reached only 81.3% even under ideal conditions, which did not reach the performance of Examples 1-1 to 1-3.

Examples 2-7 to 2-9 are obtained by changing a ratio of the membrane permeation amount of methanol and water from Examples 2-4 to 2-6, and the yield of MeOH+DME as a target product was also improved by increasing the methanol permeability 10 times. However, in a case of the $CO_2$ raw material of Example 2-7, the yield of MeOH+DME reached only 82.3% even under ideal conditions, which did not reach the performance of Examples 1-1 to 1-3.

Examples 2-10 to 2-12 are obtained by changing a ratio of the membrane permeation amount of methanol and water from Examples 2-4 to 2-6, and the yield of MeOH+DME as a target product was also improved by increasing the methanol permeability 100 times. However, in the case of the $CO_2$ raw material, the yield of MeOH+DME reached only 85.7% even under ideal conditions, which did not reach the performance of Examples 1-1 to 1-3.

Examples 2-13 to 2-15 are cases where the MeOH conversion catalyst is also disposed on the high pressure side in Examples 1-1 to 1-3. Although a catalyst was added, in the case of the $CO_2$ raw material, the yield of MeOH+DME reached only 86.8% even under ideal conditions, which did not reach the performance of Examples 1-1 to 1-3. That is, the MeOH conversion catalyst is preferably disposed only on the low pressure side.

Examples 2-16 to 2-18 are obtained by changing the ratio of the membrane permeation amount of methanol and water from Examples 1-1 to 1-3, and the yield of MeOH+DME as a target product was also significantly decreased by decreasing the methanol permeability to 1/10. For example, in the case of the $CO_2$ raw material, the yield of MeOH+DME decreased to 43.0%.

Examples 2-19 to 2-21 are obtained by changing the ratio of the membrane permeation amount of methanol and water from Examples 1-1 to 1-3, and the water permeability was increased to 1.5 times instead of decreasing the methanol permeability to 1/2. As a result, in the case of a $CO_2$ raw material, the yield of MeOH+DME decreased to 75.4%, which did not reach the performance of Examples 1-1 to Example 1-3.

In Example 2-22, in Example 1-1, the membrane permeabilities of hydrogen, CO, and $CO_2$ with respect to methanol and water were each increased by 5 times, and for example, the separation selectivity of hydrogen to methanol and water was reduced to 20 (the separation selectivity of hydrogen to methanol and water in Example 1-1 was 100). As a result, in the case of the $CO_2$ raw material, the yield of MeOH+DME decreased to 78.7%.

In Example 2-23, in Example 1-1, the membrane permeabilities of hydrogen, CO, and $CO_2$ with respect to methanol and water were each 10 times, and for example, the separation selectivity of hydrogen to methanol and water was reduced to 10. As a result, in the case of the $CO_2$ raw material, the yield of MeOH+DME decreased to 66.2%.

From the above results, the yield of MeOH+DME can be increased (preferably about 90% or more) in the case of the $CO_2$ raw material, and the usefulness of the embodiment of the $CO_2$ conversion device of the present disclosure was confirmed. In a case where CO can be easily supplied, a higher yield can be obtained in addition to the raw material gas as shown in Example 1-2 and Example 1-3.

As a result of preparing an actual apparatus and performing an actual test under each condition of Example 1-1 to Example 1-3, results equivalent to the results in Table 2 were obtained.

INDUSTRIAL APPLICABILITY

According to the present disclosure, it is possible to obtain a mixture of MeOH and DME as an intermediate from a raw material gas of $CO_2$ and hydrogen in a high yield, and as a result, it is possible to highly efficiently produce olefins and gasoline from a $CO_2$ raw material.

REFERENCE SIGNS LIST

1 $CO_2$ conversion device
2 Separation membrane
3 Methanol synthesis catalyst
4 Methanol conversion catalyst
5 Support

The invention claimed is:

1. A $CO_2$ conversion device that reacts $CO_2$ and hydrogen as raw materials to be converted to methanol and dimethyl ether, the $CO_2$ conversion device comprising:
a lamination body that is formed by laminating
a methanol synthesis catalyst;
a separation membrane;
a support that supports the separation membrane and is made from a porous substrate having a porosity; and
a methanol conversion catalyst in this order, wherein
the separation membrane is a ZSM-5 zeolite membrane having a Si/Al ratio of 10 to 20,
a reaction of $CO_2$ and hydrogen in the presence of the methanol synthesis catalyst forms methanol and water in the vicinity of an outer surface of the methanol synthesis catalyst, wherein the vicinity of the outer surface forming the methanol and water is termed as a reaction zone,
metal cations that selectively adsorb methanol and water with respect to $CO_2$ and hydrogen are immobilized on an exchange cation site of Al in a zeolite framework of the ZSM-5 zeolite,
the separation membrane is configured to allow the methanol and water to selectively permeate therethrough from the reaction zone rather than $CO_2$ or hydrogen, and
a mixture of methanol, dimethyl ether, and water is obtained by the methanol conversion catalyst.

2. The $CO_2$ conversion device according to claim 1, wherein
the support is a porous α-alumina substrate having a porosity of 25% to 55%.

3. The $CO_2$ conversion device according to claim 1, wherein
the support has a tubular shape.

4. The $CO_2$ conversion device according to claim 3, wherein
the support has a diameter of 1 to 1.6 cm and a length of 40 to 120 cm.

5. The $CO_2$ conversion device according to claim 1, wherein
the device further comprises a raw material supply means for supplying the $CO_2$ and hydrogen as raw materials to one side of the separation membrane at a pressure higher than a pressure on the other side of separation membrane,
the methanol synthesis catalyst is disposed on the high pressure side of the separation membrane, and
the methanol conversion catalyst is disposed on the low pressure side of the separation membrane.

6. An olefin and/or gasoline production system comprising the $CO_2$ conversion device according to claim 1.

7. An olefin and/or gasoline production system comprising the $CO_2$ conversion device according to claim 2.

* * * * *